(12) United States Patent
Heidelbaugh et al.

(10) Patent No.: US 8,703,745 B1
(45) Date of Patent: Apr. 22, 2014

(54) COMPOUNDS AS RECEPTOR MODULATORS WITH THERAPEUTIC UTILITY

(71) Applicant: Allergan, Inc., Irvine, CA (US)

(72) Inventors: Todd M. Heidelbaugh, Fountain Valley, AR (US); Phong X. Nguyen, Placentia, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/773,189

(22) Filed: Feb. 21, 2013

Related U.S. Application Data

(62) Division of application No. 12/951,504, filed on May 20, 2011, now Pat. No. 8,440,644.

(60) Provisional application No. 61/264,038, filed on Nov. 24, 2009.

(51) Int. Cl.
| | | |
|---|---|---|
| *A61K 31/675* | (2006.01) | |
| *A61K 31/662* | (2006.01) | |
| *C07F 9/38* | (2006.01) | |
| *A61P 27/02* | (2006.01) | |
| *A61P 3/10* | (2006.01) | |
| *A61P 29/00* | (2006.01) | |
| *A61P 11/00* | (2006.01) | |
| *A61P 1/00* | (2006.01) | |
| *A61P 37/00* | (2006.01) | |
| *A61P 9/00* | (2006.01) | |
| *A61P 17/02* | (2006.01) | |
| *A61P 25/00* | (2006.01) | |

(52) U.S. Cl.
USPC .............. 514/89; 514/92; 514/114; 546/22; 548/112; 562/11

(58) Field of Classification Search
None
See application file for complete search history.

(56) References Cited

U.S. PATENT DOCUMENTS

| | | | |
|---|---|---|---|
| 4,952,683 | A | 8/1990 | Tschannen et al. |
| 5,102,901 | A | 4/1992 | van Wijngaarden et al. |
| 5,110,987 | A | 5/1992 | Liotta et al. |
| 5,294,722 | A | 3/1994 | Kim |
| 5,403,851 | A | 4/1995 | D'Orlando et al. |
| 5,580,878 | A | 12/1996 | D'Orlando et al. |
| 6,235,912 | B1 | 5/2001 | Takesako et al. |
| 6,239,297 | B1 | 5/2001 | Takesako et al. |
| 2003/0125371 | A1 | 7/2003 | Elokdah |
| 2009/0074789 | A1* | 3/2009 | Sabbadini et al. ......... 424/155.1 |
| 2009/0312315 | A1 | 12/2009 | Yamaguchi |

FOREIGN PATENT DOCUMENTS

| | | |
|---|---|---|
| WO | 03-061567 | 7/2003 |
| WO | 03-062248 | 7/2003 |
| WO | 2008-030838 | 3/2008 |
| WO | 2008-030843 | 3/2008 |

OTHER PUBLICATIONS

Cross, L.C. et al, Rules for the Nomenclature of Organic Chemistry, Section E: Stereochemistry, Pure & Appl. Chem., 1976, 11-30, 45.

(Continued)

*Primary Examiner* — Ernst Arnold
*Assistant Examiner* — Jianfeng Song
(74) *Attorney, Agent, or Firm* — Doina G. Ene

(57) ABSTRACT

The present invention relates to novel amine derivatives, processes for preparing them, pharmaceutical compositions containing them and their use as pharmaceuticals as modulators of sphingosine-1-phosphate receptors.

2 Claims, 1 Drawing Sheet

(56) References Cited

OTHER PUBLICATIONS

Dosa, Peter et al, Solubilized Phenyl-Pyrazole Ureas as Potent, Selective 5-HT2A Inverse-Agonists and Their Application as Antiplatelet Agents, Bioorganic & Medicinal Chemistry, 2009, 5486-5489, 19.

Jeffrey J. Hale, et al., A Rational Utilization of High-Throughput Screeining Affords Selective, Orally Bioavailable 1-Benzyl-3-Carboxyazetidine, Journal of Medicinal Chemistry, Jan. 1, 2004, 6662-6665, 47 (27), US.

Stahl, Heinrich et al, Handbook of Pharmaceutical Salts, Verlag Helvetica Chimica Acta—Zurich, 2002, 329-345.

Xiong, Yifeng et al, Discovery and Structure-Activity Relationship of 3-Methoxy-N-(3-(1-methyl-1H-pyrazol-5-yl)-4-(2-morpholinoethoxy)phenyl)benzamide (APD791): A Highly Selective 5-Hydroxytryptamine2A Receptor Inverse Agonist for the Treatment of Arterial Thrombosis, J. Med. Chem., 2010, 4412-4421, 53.

Patent Cooperation Treaty, Notification of Transmittal of the International Search Report and the Written Opinion of the International Searching Authority, or the Declaration, Form PCT/ISA/220, Int. App. No. PCT/US2010/057361, Apr. 14, 2011.

Patent Cooperation Treaty, Notification of Transmittal of the International Search Report and the Written Opinion of the International Searching Authority, or the Declaration, Form PCT/ISA/220, Int. App. No. PCT/US2010/057336, Apr. 14, 2011.

Muller, Inorganic Chemistry, pp. 14-15, 1993.

Saag, Kenneth G., et al., "Teriparatide or alendronate in glucocorticoid-induced osteroporosis," (Nov. 2007) N Eng J Med; 357 (20): 2028-39, whole document.

Vippagunta, et al., "Crystalline Solids," Advanced Drug Delivery Review, 2001, 48, p. 18.

* cited by examiner

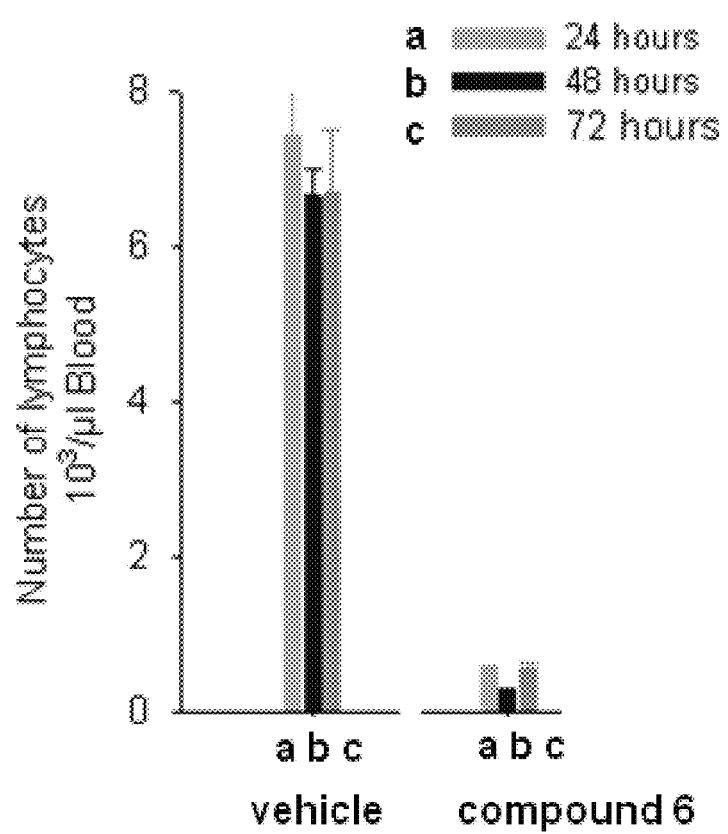

COMPOUNDS AS RECEPTOR MODULATORS WITH THERAPEUTIC UTILITY

CROSS REFERENCE TO RELATED APPLICATIONS

This application is a divisional of U.S. patent application Ser. No. 12/951,504, filed Nov. 22, 2010, which claims the benefit of U.S. Provisional Application Ser. No. 61/264,038 filed on Nov. 24, 2009, both of which are hereby incorporated by reference in their entirety.

FIELD OF THE INVENTION

The present invention relates to novel amine derivatives, processes for preparing them, pharmaceutical compositions containing them and their use as pharmaceuticals as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.
Journal of Medicinal Chemistry 2010, 53, 4412-4421 and Bioorganic & Medicinal Chemistry Letters 19 (2009) 5486-5489, describe phenyl-pyrazole derivatives as 5-HT$_{2A}$ receptor antagonists.
Patent Application US2009312315 describes phenyl-substituted carboxylic acid derivatives as PAI-1 inhibitors.

SUMMARY OF THE INVENTION

We have now discovered a group of novel compounds which are potent and selective sphingosine-1-phosphate modulators. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I, which have sphingosine-1-phosphate receptor biological activity. The compounds in accordance with the present invention are thus of use in medicine, for example in the treatment of humans with diseases and conditions that are alleviated by S1P modulation. In one aspect the invention provides a compound having Formula I or a pharmaceutically acceptable salt thereof or stereoisomeric forms thereof, or the geometrical isomers, enantiomers, diastereoisomers, tautomers, zwitterions and pharmaceutically acceptable salts thereof:

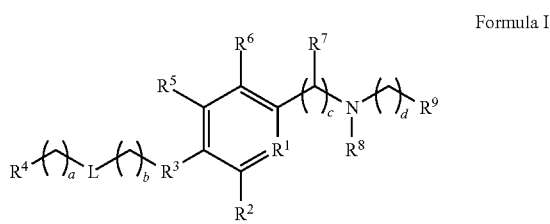

Formula I wherein:
$R^1$ is N or C—$R^{10}$;
$R^2$ is aromatic heterocycle, non-aromatic heterocycle, cycloalkyl, cycloalkenyl or aryl;
$R^3$ is O, N—$R^{11}$, CH—$R^{12}$ or S, —$CR^{13}$=$CR^{14}$—, —C(O) or —C≡O—;
$R^4$ is H, aromatic heterocycle, non-aromatic heterocycle, cycloalkyl, cycloalkenyl or aryl;
$R^5$ is H, halogen, hydroxyl, —OC$_{1-3}$ alkyl, hydroxyl or C$_{1-3}$ alkyl;
$R^6$ is H, C$_{1-3}$ alkyl, halogen, hydroxyl or —OC$_{1-3}$ alkyl;
$R^7$ is H or C$_{1-6}$ alkyl;
$R^8$ is H or C$_{1-6}$ alkyl;
$R^9$ is -OPO$_3$H$_2$, —COOH, —P(O)(OH)$_2$, —C$_{3-6}$ alkyl, —S(O)$_2$OH, —P(O)MeOH, —P(O)(H)OH or —OR$^{15}$;
$R^{10}$ is H, C$_{1-6}$ alkyl, halogen, hydroxyl or —OC$_{1-3}$ alkyl;
$R^{11}$ is H or C$_{1-3}$ alkyl;
$R^{12}$ is H, C$_{1-3}$ alkyl, halogen, hydroxyl, —OC$_{1-3}$alkyl or amino;
$R^{13}$ is H or C$_{1-3}$ alkyl;
$R^{14}$ is H or C$_{1-3}$ alkyl;
$R^{15}$ is H or C$_{1-3}$ alkyl;
L is CHR$^{16}$, O, S, NR$^{17}$ or —C(O)—;
a is 0, 1, 2, 3, 4 or 5;
b is 0, 1, 2, 3, 4 or 5;
c is 0 or 1;
d is 0, 1, 2 or 3;
$R^{16}$ is H, C$_{1-3}$ alkyl, —OC$_{1-3}$ alkyl, halogen, hydroxyl or amino, and
$R^{17}$ is H or C$_{1-3}$ alkyl;
with the provisos:
when $R^3$ is O, N—$R^{12}$, or S, and b is 0 or 1 then L is not O, S, or NR$^{17}$; and
when $R^9$ is —OPO$_3$H$_2$, —COOH, —P(O)(OH)$_2$, —S(O)$_2$OH, —P(O)MeOH or —P(O)(H)OH then d is not 0; and
when $R^9$ is —OR$^{15}$ then d is not 0 or 1.

The term "alkyl", as used herein, refers to saturated, monovalent or divalent hydrocarbon moieties having linear or branched moieties or combinations thereof and containing 1-6 carbon atom. One methylene (—CH$_2$—) group, of the alkyl can be replaced by oxygen, sulfur, sulfoxide, nitrogen, carbonyl, carboxyl, sulfonyl, or by a divalent C$_{3-6}$ cycloalkyl. Alkyl groups can be substituted by halogen, hydroxyl, cycloalkyl, amino, non-aromatic heterocycles, carboxylic acid, phosphonic acid groups, sulphonic acid groups, phosphoric acid.

The term "cycloalkyl", as used herein, refers to a monovalent or divalent group of 3 to 8 carbon atoms, preferably 3 to 5 carbon atoms derived from a saturated cyclic hydrocarbon. Cycloalkyl groups can be monocyclic or polycyclic. Cycloalkyl can be substituted by 1 to 3 $C_{1-3}$ alkyl groups or 1 or 2 halogens. Cycloalkyl group in the present case is cyclopentane.

The term "cycloalkenyl", as used herein, refers to a monovalent or divalent group of 3 to 8 carbon atoms, preferably 3 to 6 carbon atoms derived from a saturated cycloalkyl having one double bond. Cycloalkenyl groups can be monocyclic or polycyclic. Cycloalkenyl groups can be substituted by 1 to 3 $C_{1-3}$ alkyl groups or 1 or 2 halogens. Cycloalkenyl group in the present case is cyclopentene.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by 1 to 2 $C_{1-3}$ alkyl.

The term "alkynyl", as used herein, refers to a monovalent or divalent hydrocarbon radical having 2 to 6 carbon atoms, derived from a saturated alkyl, having at least one triple bond.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. The heterocyclic ring can be saturated or non-saturated. The heterocyclic ring can be interrupted by a C=O; the S heteroatom can be oxidized. Heterocycles can be monocyclic or polycyclic. Heterocyclic ring moieties can be substituted by hydroxyl, 1 to 2 $C_{1-3}$ alkyl or 1 to 2 halogens. Usually heterocyclic groups are 5 or 6 membered rings. Usually in the present case heterocyclic groups are pyridine, pyrazol, pyrazolidine, pyrroline, pyrrolidine, imidazoline, pyrazoline, thiazoline, oxazoline, thiophene, dihydrothiophene, furan, dihydrofuran, pyrrole, pyrroline, oxazole, thiazole, imidazole, pyrazole, pyrazoline, isoxazole, isothiazole, tetrazole, oxadiazole, 1,2,5-oxadiazole, thiadiazole, 1,2,3-triazole, 1,2,4-triazole, imidazole, imidazoline, pyrrolidinone, pyrrol-2(3H)-one, imidazolidin-2-one, or 1,2,4-triazol-5(4H)-one.

The term "aryl" as used herein, refers to an organic moiety derived from an aromatic hydrocarbon consisting of a ring containing 6 to 10 carbon atoms by removal of one hydrogen, which can be substituted by 1 to 3 halogen atoms or by 1 to 2 $C_{1-3}$ alkyl groups. Usually aryl is phenyl.

The group of formula "—$CR^{13}$=$CR^{14}$—", as used herein, represents an alkenyl radical.

The group of formula "—C≡C—", as used herein, represents an alkynyl radical.

The term "hydroxyl" as used herein, represents a group of formula "—OH".

The term "carbonyl" as used herein, represents a group of formula "—C=O".

The term "carboxyl" as used herein, represents a group of formula "—C(O)O—".

The term "sulfonyl" as used herein, represents a group of formula "—$SO_2$".

The term "sulfate" as used herein, represents a group of formula "—O—$S(O)_2$—O—".

The term "carboxylic acid" as used herein, represents a group of formula "—C(O)OH".

The term "sulfoxide" as used herein, represents a group of formula "—S=O".

The term "phosphonic acid" as used herein, represents a group of formula "—$P(O)(OH)_2$".

The term "phosphoric acid" as used herein, represents a group of formula "—$(O)P(O)(OH)_2$".

The term "boronic acid", as used herein, represents a group of formula "—$B(OH)_2$".

The term "sulphonic acid" as used herein, represents a group of formula "—$S(O)_2OH$".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Generally $R^1$ is N or C—$R^{10}$.

Generally $R^2$ is aromatic heterocycle, non-aromatic heterocycle, cycloalkyl, cycloalkenyl or aryl. Usually, in the present case, $R^2$ is aromatic heterocycle or cycloalkenyl. Usually aromatic heterocyclic rings are 5 membered rings. Preferred $R^2$ are pyrazol, pyrazolidine, pyrroline, pyrrolidine, imidazoline, pyrazoline, thiazoline, oxazoline, thiophene, dihydrothiophene, furan, dihydrofuran, pyrrole, pyrroline, oxazole, thiazole, imidazole, pyrazole, pyrazoline, isoxazole, isothiazole, tetrazole, oxadiazole, 1,2,5-oxadiazole, thiadiazole, 1,2,3-triazole, 1,2,4-triazole, imidazole, imidazoline, pyrrolidinone, pyrrol-2(3H)-one, imidazolidin-2-one, or 1,2,4-triazol-5(4H)-one.

Generally $R^3$ is O, N—$R^{11}$, CH—$R^{12}$, S, —$CR^{13}$=$CR^{14}$—, —C(O) or —C≡C—. Usually, in the present case, $R^3$ is O.

Generally $R^4$ is H, aromatic heterocycle, non-aromatic heterocycle, cycloalkyl or aryl. Usually, in the present case, $R^4$ is aryl or H.

Generally $R^5$ is H, halogen, —$OC_{1-3}$ alkyl, hydroxyl or $C_{1-3}$ alky. Usually, in the present case, $R^5$ is H.

Generally $R^6$ is H, $C_{1-3}$ alkyl, halogen, hydroxyl or —$OC_{1-3}$ alkyl. Usually, in the present case, $R^6$ is H.

Generally $R^7$ is H or $C_{1-6}$ alkyl. Usually, in the present case, $R^7$ is H.

Generally $R^8$ is H or $C_{1-6}$ alkyl. Usually, in the present case, $R^8$ is H.

Generally $R^9$ is $OPO_3H_2$, COOH, $P(O)(OH)_2$, $C_{3-6}$ alkyl, —$S(O)_2OH$, —P(O)MeOH, —P(O)(H)OH or —$OR^{15}$. Usually, in the present case, $R^9$ is $P(O)(OH)_2$.

Generally $R^{10}$ is H, $C_{1-6}$ alkyl, halogen, hydroxyl or —$OC_{1-3}$ alkyl. Usually, in the present case, $R^{10}$ is H.

Generally $R^{11}$ is H or $C_{1-3}$ alkyl.

Generally $R^{12}$ is H or $C_{1-3}$ alkyl

Generally $R^{13}$ is H or $C_{1-3}$ alkyl.

Generally $R^{14}$ is H or $C_{1-3}$ alkyl.

Generally $R^{15}$ is H or $C_{1-3}$ alkyl.

Generally a is 0, 1, 2, 3, 4 or 5. Usually, in the present case, a is 1, 2, 3, 4 or 5.

Generally b is 0, 1, 2, 3, 4 or 5. Usually, in the present case, b is 1, 2, 3 or 4.

Generally c is 0 or 1. Usually, in the present case, c is 1.

Generally d is 0, 1, 2 or 3. Usually, in the present case, d is 3.

Generally L is $CHR^{17}$, O, S or $NR^{17}$. Usually, in the present case, L is $CHR^{16}$.

Generally $R^{16}$ is H, $C_{1-3}$ alkyl, —$OC_{1-3}$ alkyl, halogen, hydroxyl, amino. Usually, in the present case, $R^{16}$ is H.

Generally $R^{17}$ is H or $C_{1-3}$ alkyl.

In one embodiment of the invention $R^1$ is N or C—$R^{10}$;

$R^2$ is aromatic heterocycle or cycloalkenyl;

$R^3$ is O, N—$R^{11}$, CH—$R^{12}$ or S, —$CR^{13}$=$CR^{14}$—, —C(O) or —C≡O—;

$R^4$ is H, aromatic heterocycle, non-aromatic heterocycle, cycloalkyl, cycloalkenyl or aryl;
$R^5$ is H, halogen, hydroxyl, —$OC_{1-3}$ alkyl, hydroxyl or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H or $C_{1-6}$ alkyl;
$R^9$ is —$OPO_3H_2$, —COOH, —$P(O)(OH)_2$, —$C_{3-6}$ alkyl, —$S(O)_2OH$, —P(O)MeOH, —P(O)(H)OH or —$OR^{15}$;
$R^{10}$ is H, $C_{1-6}$ alkyl, halogen, hydroxyl or —$OC_{1-3}$ alkyl;
$R^{11}$ is H or $C_{1-3}$ alkyl;
$R^{12}$ is H, $C_{1-3}$ alkyl, halogen, hydroxyl, —$OC_{1-3}$alkyl or amino;
$R^{13}$ is H or $C_{1-3}$ alkyl;
$R^{14}$ is H or $C_{1-3}$ alkyl;
$R^{15}$ is H or $C_{1-3}$ alkyl;
L is $CHR^{16}$, O, S, $NR^{17}$ or —C(O)—;
a is 0, 1, 2, 3, 4 or 5;
b is 0, 1, 2, 3, 4 or 5;
c is 0 or 1;
d is 0, 1, 2 or 3;
$R^{16}$ is H, $C_{1-3}$ alkyl, —$OC_{1-3}$ alkyl, halogen, hydroxyl or amino; and
$R^{17}$ is H or $C_{1-3}$ alkyl;
with the provisos
when $R^3$ is O, N—$R^{12}$, or S, and b is 0 or 1 then L is not O, S, or $NR^{17}$; and
when $R^9$ is —$OPO_3H_2$, —COOH, —$P(O)(OH)_2$, —$S(O)_2OH$, —P(O)MeOH or —P(O)(H)OH then
d is not 0; and
when $R^9$ is —$OR^{15}$ then d is not 0 or 1.

In another embodiment of the invention
$R^1$ is N or C—$R^{10}$;
$R^2$ is 5-member aromatic heterocycle or cycloalkenyl;
$R^3$ is O, N—$R^{11}$, CH—$R^{12}$ or S, —$CR^{13}$=$CR^{14}$—, —C(O) or —C≡O—;
$R^4$ is H, aromatic heterocycle, non-aromatic heterocycle, cycloalkyl, cycloalkenyl or aryl;
$R^5$ is H, halogen, hydroxyl, —$OC_{1-3}$ alkyl, hydroxyl or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H or $C_{1-6}$ alkyl;
$R^9$ is —$OPO_3H_2$, —COOH, —$P(O)(OH)_2$, —$C_{3-6}$ alkyl, —$S(O)_2OH$, —P(O)MeOH, —P(O)(H)OH or —$OR^{15}$;
$R^{10}$ is H, $C_{1-6}$ alkyl, halogen, hydroxyl or —$OC_{1-3}$ alkyl;
$R^{11}$ is H or $C_{1-3}$ alkyl;
$R^{12}$ is H, $C_{1-3}$ alkyl, halogen, hydroxyl, —$OC_{1-3}$alkyl or amino;
$R^{13}$ is H or $C_{1-3}$ alkyl;
$R^{14}$ is H or $C_{1-3}$ alkyl;
$R^{15}$ is H or $C_{1-3}$ alkyl;
L is $CHR^{16}$, O, S, $NR^{17}$ or —C(O)—;
a is 0, 1, 2, 3, 4 or 5;
b is 0, 1, 2, 3, 4 or 5;
c is 0 or 1;
d is 0, 1, 2 or 3;
$R^{16}$ is H, $C_{1-3}$ alkyl, —$OC_{1-3}$ alkyl, halogen, hydroxyl or amino, and
$R^{17}$ is H or $C_{1-3}$ alkyl;
with the provisos:
when $R^3$ is O, N—$R^{12}$, or S, and b is 0 or 1 then L is not O, S, or $NR^{17}$; and
when $R^9$ is —$OPO_3H_2$, —COOH, —$P(O)(OH)_2$, —$S(O)_2OH$, —P(O)MeOH or —P(O)(H)OH then
d is not 0; and
when $R^9$ is —$OR^{15}$ then d is not 0 or 1.

In another embodiment of the invention
$R^1$ is N or C—$R^{10}$;
$R^2$ is cyclopentane, cyclopentene, pyrazolidine, pyrroline, pyrrolidine, imidazoline, pyrazoline, thiazoline, oxazoline, thiophene, dihydrothiophene, furan, dihydrofuran, pyrrole, pyrroline, pyrrolidine, oxazole, oxazoline, thiazole, imidazole, pyrazole, pyrazoline, isoxazole, isothiazole, tetrazole, oxadiazole, 1,2,5-oxadiazole, thiadiazole, 1,2,3-triazole, 1,2,4-triazole, imidazole, imidazoline, pyrrolidinone, pyrrol-2 (3H)-one, imidazolidin-2-one, or 1,2,4-triazol-5(4H)-one;
$R^3$ is O, N—$R^{11}$, CH—$R^{12}$ or S, —$CR^{13}$=$CR^{14}$—, —C(O) or —C≡O—;
$R^4$ is H, aromatic heterocycle, non-aromatic heterocycle, cycloalkyl, cycloalkenyl or aryl;
$R^5$ is H, halogen, hydroxyl, —$OC_{1-3}$ alkyl, hydroxyl or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H or $C_{1-6}$ alkyl;
$R^9$ is —$OPO_3H_2$, —COOH, —$P(O)(OH)_2$, —$C_{3-6}$ alkyl, —$S(O)_2OH$, —P(O)MeOH, —P(O)(H)OH or —$OR^{15}$;
$R^{10}$ is H, $C_{1-6}$ alkyl, halogen, hydroxyl or —$OC_{1-3}$ alkyl;
$R^{11}$ is H or $C_{1-3}$ alkyl;
$R^{12}$ is H, $C_{1-3}$ alkyl, halogen, hydroxyl, —$OC_{1-3}$alkyl or amino;
$R^{13}$ is H or $C_{1-3}$ alkyl;
$R^{14}$ is H or $C_{1-3}$ alkyl;
$R^{15}$ is H or $C_{1-3}$ alkyl;
L is $CHR^{16}$, O, S, $NR^{17}$ or —C(O)—;
a is 0, 1, 2, 3, 4 or 5;
b is 0, 1, 2, 3, 4 or 5;
c is 0 or 1;
d is 0, 1, 2 or 3;
$R^{16}$ is H, $C_{1-3}$ alkyl, —$OC_{1-3}$ alkyl, halogen, hydroxyl or amino, and
$R^{17}$ is H or $C_{1-3}$ alkyl;
with the provisos:
when $R^3$ is O, N—$R^{12}$, or S, and b is 0 or 1 then L is not O, S, or $NR^{17}$; and
when $R^9$ is —$OPO_3H_2$, —COOH, —$P(O)(OH)_2$, —$S(O)_2OH$, —P(O)MeOH or —P(O)(H)OH then
d is not 0; and
when $R^9$ is —$OR^{15}$ then d is not 0 or 1.

In another embodiment of the invention
$R^1$ is N or C—$R^{10}$;
$R^2$ is 5-member aromatic heterocycle or cycloalkenyl;
$R^3$ is O, N—$R^{11}$, CH—$R^{12}$ or S, —$CR^{13}$=$CR^{14}$—, —C(O) or —C≡O—;
$R^4$ is H, aromatic heterocycle, non-aromatic heterocycle, cycloalkyl, cycloalkenyl or aryl;
$R^5$ is H, halogen, hydroxyl, —$OC_{1-3}$ alkyl, hydroxyl or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H or $C_{1-6}$ alkyl;
$R^9$ is —$OPO_3H_2$, or —$OR^{15}$;
$R^{10}$ is H, $C_{1-6}$ alkyl, halogen, hydroxyl or —$OC_{1-3}$ alkyl;
$R^{11}$ is H or $C_{1-3}$ alkyl;
$R^{12}$ is H, $C_{1-3}$ alkyl, halogen, hydroxyl, —$OC_{1-3}$alkyl or amino;
$R^{13}$ is H or $C_{1-3}$ alkyl;
$R^{14}$ is H or $C_{1-3}$ alkyl;
$R^{15}$ is H or $C_{1-3}$ alkyl;
L is $CHR^{16}$, O, S, $NR^{17}$ or —C(O)—;
a is 0, 1, 2, 3, 4 or 5;
b is 0, 1, 2, 3, 4 or 5;
c is 0 or 1;

d is 1, 2 or 3;
$R^{16}$ is H, $C_{1-3}$ alkyl, —$OC_{1-3}$ alkyl, halogen, hydroxyl or amino, and
$R^{17}$ is H or $C_{1-3}$ alkyl;
with the provisos:
when $R^3$ is O, N—$R^{12}$, or S, and b is 0 or 1 then L is not O, S, or $NR^{17}$; and
when $R^9$ is —$OR^{15}$ then d is not 1.

In another embodiment of the invention
$R^1$ is N or C—$R^{10}$;
$R^2$ is 5-member aromatic heterocycle or cycloalkenyl;
$R^3$ is O, N—$R^{11}$, CH—$R^{12}$ or S, —$CR^{13}$=$CR^{14}$—, —C(O) or —C=O—;
$R^4$ is H, aromatic heterocycle, non-aromatic heterocycle, cycloalkyl, cycloalkenyl or aryl;
$R^5$ is H, halogen, hydroxyl, —$OC_{1-3}$ alkyl, hydroxyl or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H or $C_{1-6}$ alkyl;
$R^9$ is —P(O)(OH)$_2$, —P(O)MeOH, or —P(O)(H)OH;
$R^{10}$ is H, $C_{1-6}$ alkyl, halogen, hydroxyl or —$OC_{1-3}$ alkyl;
$R^{11}$ is H or $C_{1-3}$ alkyl;
$R^{12}$ is H, $C_{1-3}$ alkyl, halogen, hydroxyl, —$OC_{1-3}$alkyl or amino;
$R^{13}$ is H or $C_{1-3}$ alkyl;
$R^{14}$ is H or $C_{1-3}$ alkyl;
$R^{15}$ is H or $C_{1-3}$ alkyl;
L is $CHR^{16}$, O, S, $NR^{17}$ or —C(O)—;
a is 0, 1, 2, 3, 4 or 5;
b is 0, 1, 2, 3, 4 or 5;
c is 0 or 1;
d is 1, 2 or 3;
$R^{16}$ is H, $C_{1-3}$ alkyl, —$OC_{1-3}$ alkyl, halogen, hydroxyl or amino, and
$R^{17}$ is H or $C_{1-3}$ alkyl;
with the proviso:
when $R^3$ is O, N—$R^{12}$, or S, and b is 0 or 1 then L is not O, S, or $NR^{17}$.

In another embodiment of the invention
$R^1$ is N or C—$R^{10}$;
$R^2$ is 5-member aromatic heterocycle or cycloalkenyl;
$R^3$ is O, N—$R^{11}$, CH—$R^{12}$ or S, —$CR^{13}$=$CR^{14}$—, —C(O) or —C=O—;
$R^4$ is H, aromatic heterocycle, non-aromatic heterocycle, cycloalkyl, cycloalkenyl or aryl;
$R^5$ is H, halogen, hydroxyl, —$OC_{1-3}$ alkyl, hydroxyl or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H or $C_{1-6}$ alkyl;
$R^9$ is —COOH, —S(O)$_2$OH or —$C_{3-6}$ alkyl;
$R^{10}$ is H, $C_{1-6}$ alkyl, halogen, hydroxyl or —$OC_{1-3}$ alkyl;
$R^{11}$ is H or $C_{1-3}$ alkyl;
$R^{12}$ is H, $C_{1-3}$ alkyl, halogen, hydroxyl, —$OC_{1-3}$alkyl or amino;
$R^{13}$ is H or $C_{1-3}$ alkyl;
$R^{14}$ is H or $C_{1-3}$ alkyl;
$R^{15}$ is H or $C_{1-3}$ alkyl;
L is $CHR^{16}$, O, S, $NR^{17}$ or —C(O)—;
a is 0, 1, 2, 3, 4 or 5;
b is 0, 1, 2, 3, 4 or 5;
c is 0 or 1;
d is 1, 2 or 3;
$R^{16}$ is H, $C_{1-3}$ alkyl, —$OC_{1-3}$ alkyl, halogen, hydroxyl or amino, and
$R^{17}$ is H or $C_{1-3}$ alkyl;
with the proviso:
when $R^3$ is O, N—$R^{12}$, or S, and b is 0 or 1 then L is not O, S, or $NR^{17}$.

In another embodiment of the invention
$R^1$ is N or C—$R^{10}$; and
$R^2$ is aromatic heterocycle, non-aromatic heterocycle or cycloalkenyl; and
$R^3$ is O; and
$R^4$ is aryl or H; and
$R^5$ is H; and
$R^6$ is H; and
$R^7$ is H; and
$R^8$ is H; and
$R^9$ is P(O)(OH)$_2$; and
$R^{10}$ is H; and
a is 1, 2, 4 or 5; and
b is 1, 2 or 4; and
c is 1; and
d is 3; and
L is $CHR^{16}$; and
$R^{16}$ is H.

In another embodiment of the invention
$R^1$ is N or C—$R^{10}$; and
$R^2$ is aromatic heterocycle, non-aromatic heterocycle or cycloalkenyl; and
$R^3$ is O; and
$R^4$ is aryl; and
$R^5$ is H; and
$R^6$ is H; and
$R^7$ is H; and
$R^8$ is H; and
$R^9$ is P(O)(OH)$_2$; and
$R^{10}$ is H; and
a is 1 or 2; and
b is 1 or 2; and
c is 1; and
d is 3; and
L is $CHR^{16}$; and
$R^{16}$ is H.

In another embodiment of the invention
$R^1$ is N; and
$R^2$ is aromatic heterocycle, non-aromatic heterocycle or cycloalkenyl; and
$R^3$ is O; and
$R^4$ is aryl; and
$R^5$ is H; and
$R^6$ is H; and
$R^7$ is H; and
$R^8$ is H; and
$R^9$ is P(O)(OH)$_2$; and
a is 1 or 2; and
b is 1 or 2; and
c is 1; and
d is 3; and
L is $CHR^{16}$; and
$R^{16}$ is H.

In another embodiment of the invention
$R^1$ is C—$R^{10}$; and
$R^2$ is aromatic heterocycle, non-aromatic heterocycle or cycloalkenyl; and
$R^3$ is O; and
$R^4$ is H; and
$R^5$ is H; and
$R^6$ is H; and
$R^7$ is H; and
$R^8$ is H; and $R^9$ is $P(O)(OH)_2$; and
$R^{10}$ is H; and
a is 2, 3, 4 or 5; and
b is 2, 3, 4 or 5; and
c is 1; and
d is 3; and
L is $CHR^{16}$; and
$R^{16}$ is H.

Compounds of the invention are:

[3-({3-(2-furyl)-4-[(5-phenylpentyl)oxy]benzyl}amino)propyl]phosphonic acid;

[3-({3-(1,3-oxazol-2-yl)-4-[(5-phenylpentyl)oxy]benzyl}amino)propyl]phosphonic acid;

[3-({4-[(5-phenylpentyl)oxy]-3-(1,3-thiazol-2-yl)benzyl}amino)propyl]phosphonic acid;

[3-({3-(3-furyl)-4-[(5-phenylpentyl)oxy]benzyl}amino)propyl]phosphonic acid;

[3-({4-[(5-phenylpentyl)oxy]-3-(3-thienyl)benzyl}amino)propyl]phosphonic acid;

[3-({4-[(5-phenylpentyl)oxy]-3-(2-thienyl)benzyl}amino)propyl]phosphonic acid;

[3-({4-[3-(4-isobutylphenyl)propoxy]-3-(2-thienyl)benzyl}amino)propyl]phosphonic acid;

[3-({3-cyclopent-1-en-1-yl-4-[(5-phenylpentyl)oxy]benzyl}amino)propyl]phosphonic acid;

{3-[({6-(3-furyl)-5-[(5-phenylpentyl)oxy]pyridin-2-yl}methyl)amino]propyl}phosphonic acid;

{3-[({5-[(5-phenylpentyl)oxy]-6-(2-thienyl)pyridin-2-yl}methyl)amino]propyl}phosphonic acid;

(3-{[4-(nonyloxy)-3-(2-thienyl)benzyl]amino}propyl)phosphonic acid;

(3-{[4-(decyloxy)-3-(2-thienyl)benzyl]amino}propyl)phosphonic acid;

3-({3-(5-fluoro-2-thienyl)-4-[(5-phenylpentyl)oxy]benzyl}amino)propyl]phosphonic acid;

2-({4-[(5-phenylpentyl)oxy]-3-(2-thienyl)benzyl}amino)ethyl dihydrogen phosphate;

3-({4-[(5-phenylpentyl)oxy]-3-(2-thienyl)benzyl}amino)propane-1-sulfonic acid;

methyl[3-({4-[(5-phenylpentyl)oxy]-3-(2-thienyl)benzyl}amino)propyl]phosphinic acid;

2-({4-[(5-phenylpentyl)oxy]-3-(2-thienyl)benzyl}amino)propan-1-ol;

2-({4-[(5-phenylpentyl)oxy]-3-(2-thienyl)benzyl}amino)propane-1,3-diol.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, a hydrohalic acid such as hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically. Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation: not limited to the treatment of diabetic retinopathy, other retinal degenerative conditions, dry eye, angiogenesis and wounds.

Therapeutic utilities of S1P modulators are ocular diseases, such as but not limited to: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases such as but not limited to: various inflammatory diseases, including acute lung injury, its prevention, sepsis, tumor metastasis, atherosclerosis, pulmonary edemas, and ventilation-induced lung injury; or autoimmune diseases and immunosuppression such as but not limited to: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermitis, and organ transplantation; or allergies and other inflammatory diseases such as but not limited to: urticaria, bronchial asthma, and other airway inflammations including pulmonary emphysema and chronic obstructive pulmonary diseases; or cardiac protection such as but not limited to: ischemia reperfusion injury and atherosclerosis; or wound healing such as but not limited to: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation such as but not limited to: treatment of osteoporosis and various bone fractures including hip and ankles; or antinociceptive activity such as but not limited to: visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular disease, wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases, various inflammatory diseases, including acute lung injury, its prevention, sepsis, tumor metastasis, atherosclerosis, pulmonary edemas, and ventilation-induced lung injury; or autoimmune diseases and immunosuppression, rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation; or allergies and other inflammatory diseases, urticaria, bronchial asthma, and other airway inflammations including pulmonary emphysema and chronic obstructive pulmonary diseases; or cardiac protection, ischemia reperfusion injury and atherosclerosis; or wound healing, scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation, treatment of osteoporosis and various bone fractures including hip and ankles; or anti-nociceptive activity, visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier therefore. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The synthetic schemes set forth below, illustrate how compounds according to the invention can be made. Those skilled in the art will be able to routinely modify and/or adapt the following scheme to synthesize any compounds of the invention covered by Formula I.

In Scheme 1, hydroxybenzaldehydes react with hydroxylated compounds in the presence of triphenylphosphine and diethyl azodicarboxylate to give the corresponding ether intermediate. This intermediate is coupled with the boronic acid or the stannate of the corresponding $R^2$ group to give the corresponding intermediate. This intermediate reacts with 3-aminopropylphosphonic acid to give a derivative of Formula I.

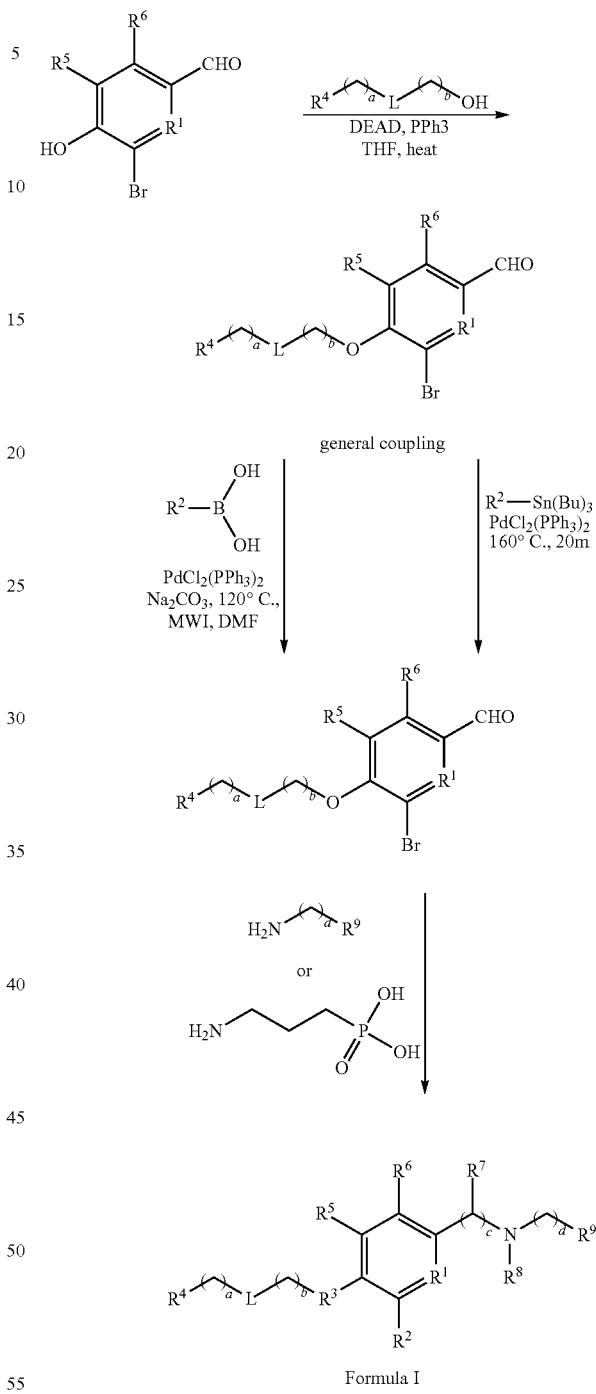

In Scheme 2, picolinaldehydes react with brominated compounds in the presence of potassium carbonate to give the corresponding intermediate. This intermediate is coupled with the boronic acid of the corresponding $R^2$ group to give the corresponding intermediate, which reacts with 3-aminopropylphosphonic acid to give a derivative of Formula I.

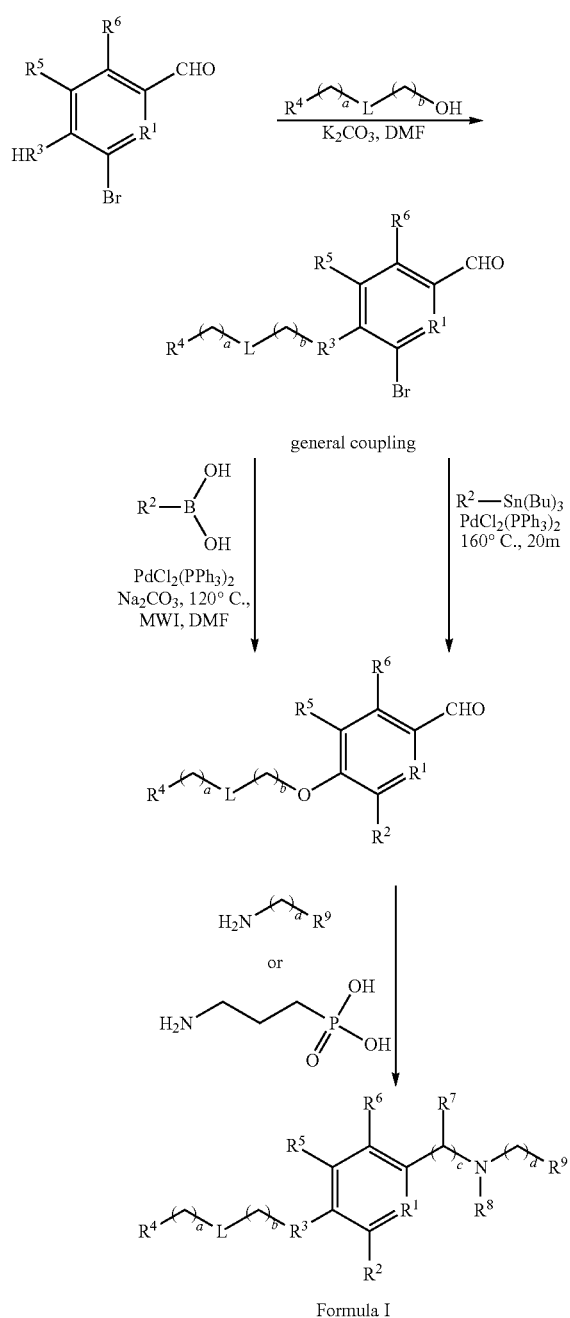

Scheme 2

$R^1$ is CH
$R^3$ is O
c is 1
d is 3

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

Compound names were generated with ACD version 8; and Intermediates and reagent names used in the examples were generated with software such as Chem Bio Draw Ultra version 12.0 or Auto Nom 2000 from MDL ISIS Draw 2.5 SP1.

In general, characterization of the compounds is performed according to the following methods:

NMR spectra are recorded on 300 and/or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, AscentScientific LLC., Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

The following abbreviations are used in the examples:
s, m, h, d second, minute, hour, day
$NH_3$ ammonia
$CH_3CN$ acetonitrile
PSI pound per square inch
DCM dichloromethane
DMF N,N-dimethylformamide
NaOH sodium hydroxide
MeOH methanol
$CD_3OD$ deuterated methanol
$NH_3$ ammonia
HCl hydrochloric acid Na₂SO₄ sodium sulfate
rt room temperature
DMF dimethylformamide
MgSO₄ magnesium sulfate
EtOAc ethyl acetate
CDCl₃ deuterated chloroform
DMSO-d₆ deuterated dimethyl sulfoxide
Auto-column automated flash liquid chromatography
TFA trifluoroacetic acid
THF tetrahydrofuran
NaHB(OAc)₃ sodium triacetoxyborohydride
DEAD diethyl azodicarboxylate
Na₂CO₃ sodium carbonate
Cs₂CO₃ cesium carbonate
M molar
PdCl₂(PPh₃)₂ bis(triphenylphosphine)palladium(II) chloride
AcOH acetic acid
K₂CO₃ potassium carbonate
CuI copper iodide
MnO₂ magnesiunm oxide
MgCl₂ magnesium chloride
NaCl sodium chloride
Ti(OEt)₄ titanium ethoxide
MeMgBr methylmagnesium bromide
CHCl₃ chloroform
TBAH tetrabutylammonium hydroxide The following synthetic schemes illustrate how compounds according to the invention can be made. Those skilled in the art will be routinely able to modify and/or adapt the following schemes to synthesize any compound of the invention covered by Formula I.

Some compounds of this invention can generally be prepared in one step from commercially available literature starting materials.

Example 1

Compound 1

[3-({3-(2-furyl)-4-[(5-phenylpentyl)oxy]benzyl}amino)propyl]phosphonic acid

Step-1:

A solution of 5-phenyl-pentan-1-ol [CAS 10521-91-2] (4.50 mL, 26.6 mmol), 3-bromo-4-hydroxybenzaldehyde [CAS 2973-78-6] (5.36 g, 26.7 mmol), triphenylphosphine (9.1 g, 34.6 mmol) and DEAD, (14.5 mL, 40% in toluene, ~1.2 eqv) in THF (100 mL) was reacted at rt for 1 h, followed by heating to 60° C. for 2 days. Silica gel was added and the solvents were removed under vacuum. Auto-column: chromatography on an Teledyne-ISCO CombiFlash with a silica column with 9.5 hexane/0.5 EtOAC to 9 Hexanes/1 EtOAc gave Intermediate 1 as a clear oil that solidified upon standing, 5.38 g (58%): 3-bromo-4-(5-phenyl-pentyloxy)-benzaldehyde.

$^1$H NMR (300 MHz, CDCl₃): δ 9.83 (s, 1H), 8.07 (d, J=2.1 Hz, 1H), 7.78 (dd, J=8.7, 2.1 Hz, 1H), 7.28-7.18 (m, 5H), 6.96 (d, J=8.4 Hz, 1H), 4.11 (t, J=6.3 Hz, 2H), 2.67 (t, J=7.2 Hz, 2H), 1.92-1.55 (m, 6H).

Step-2:

Intermediate 1 (0.65 g, 1.87 mmol) in DMF (14 mL) was reacted with tributyl(furan-2-yl)stannane [CAS 118486-94-5] (1.2 mL, 3.70 mmol) and PdCl₂(PPh₃)₂ (0.197 g, ~15 mol %) at 160° C. for 15 m with MWI (microwave irradiation: Biotage Initiator 2.5). The reaction mixture was diluted with 2:1 EtOAc/Hexanes (~150 mL), washed with water (3×), and dried over MgSO₄, filtered and concentrated onto silica gel. Auto-column (9.5 hexane/0.5 EtOAc) gave Intermediate 2: 3-furan-2-yl-4-(5-phenyl-pentyloxy)-benzaldehyde as a white solid, 0.44 g (70%).

$^1$H NMR (300 MHz, CDCl₃): δ 9.94 (s, 1H), 8.37 (d, J=2.1 Hz, 1H), 7.77-7.74 (m, 1H), 7.49 (d, J=1.2 Hz, 1H), 7.30-7.10 (m, 5H), 7.04-6.90 (m, 2H), 6.50 (brs, 1H), 4.21-4.05 (m, 2H), 2.70-2.60 (m, 2H), 2.10-1.50 (series m, 6H).

Step 3:

3-Aminopropylphosphonic acid [CAS 13138-33-5](225 mg, 1.57 mmol) in MeOH (15 mL) followed by tetrabutylammonium hydroxide (TBAH) (12.8 mL, ~12.8 mmol, 1.0M in MeOH) at 50° C. for ~1 h. Intermediate 2 (440 mg, 1.31 mmol) in THF (3 mL) and MeOH (6 mL) was added, and after 30 m at 50° C. the mixture was cooled to rt. Sodium borohydride (120 mg, 3.17 mmol) was added and the reaction was continued until complete (1-2 h). [Alternative procedure: use of tetrabutylammonium hydroxide (3 eqv.) following with sodium borohydride (1.5 eqv.) at rt for ~16-18 h.] The solvent was removed under vacuum and water was added, followed by HCl (2M) until pH 2-4. The aqueous layer was extracted (two times) with chloroform:isopropanol (~3:1). The organic layers were dried over MgSO₄, filtered and concentrated onto amine-silica gel (ISCO). Auto-column (amine-silica gel column) (70% MeOH, 29.5% CH₂Cl₂, 0.5% AcOH) gave the title compound [3-({3-(2-furyl)-4-[(5-phenylpentyl)oxy]benzyl}amino)propyl]phosphonic acid as a white solid. 310 mg, (52%)

$^1$H NMR (600 MHz, CF₃CO₂D): δ 7.83-7.82 (m, 1H), 7.38-7.30 (m, 2H), 7.20-7.17 (m, 3H), 7.13 (d, J=7.8 Hz, 2H), 7.08 (t, J=6.6 Hz, 1H), 7.00 (dd, J=2.4, 8.4 Hz, 1H), 6.41 (d, J=3.0 Hz, 1H), 4.30 (s, 2H), 4.14-4.11 (m, 2H), 3.40 (brs, 2H), 2.62 (t, J=7.8 Hz, 2H), 2.24-2.19 (m, 2H), 2.14-2.09 (m, 2H), 1.95-1.90 (m, 2H), 1.73-1.69 (m, 2H), 1.57-1.55 (m, 2H).

Compounds 2 and 3 were prepared from the corresponding benzaldehyde, stannate and 3-Aminopropylphosphonic acid in a similar manner to the procedure described in Example 1 for Compound 1. The reagents used and the results are described below in Table 1.

TABLE 1

| Compound number | IUPAC name | Reagent(s) used | $^1$H NMR δ (ppm) for Compound |
|---|---|---|---|
| 2 | [3-({3-(1,3-oxazol-2-yl)-4-[(5-phenylpentyl)oxy]benzyl}amino)propyl]phosphonic acid | 2-(tributylstannyl)oxazole [CAS 145214-05-7] | $^1$H NMR (600 MHz, CF₃CO₂D): δ 8.10 (d, J = 1.8 Hz, 1H), 7.94 (d, J = 1.8 Hz, 1H), 7.72 (d, J = 9.0 Hz, 1H), 7.47 (d, J = 1.8 Hz, 1H), 7.16 (d, J = 9.0 Hz, 1H), 7.01-6.98 (m, 2H), 6.93-6.90 (m, 3H), 4.26-4.24 (m, 4H), 3.30 (brs, 2H), 2.44 (t, J = 7.2 Hz, 2H), 2.11-2.07 (m, 2H), 1.98-1.94 (m, 2H), 1.81-1.76 (m, 2H), 1.56-1.51 (m, 2H), 1.31-1.27 (m, 2H). |
| 3 | [3-({4-[(5-phenylpentyl)oxy]-3-(1,3-thiazol-2-yl)benzyl}amino)propyl]phosphonic acid | 2-(tributylstannyl)thiazole [CAS 121359-48-6] | $^1$H NMR (600 MHz, CF₃CO₂D): δ 8.38 (brs, 1H), 8.19 (q, J = 1.8 Hz, 1H), 8.01-7.99 (m, 2H), 7.51 (dd, J = 1.8, 9.0 Hz, 1H), 7.41-7.38 (m, 2H), 7.34 (d, J = 7.8 Hz, 2H), 7.32- |

TABLE 1-continued

| Compound number | IUPAC name | Reagent(s) used | $^1$H NMR δ (ppm) for Compound |
|---|---|---|---|
| | | | 7.29 (m, 1H), 4.62 (brs, 2H), 4.58 (t, J = 6.0 Hz, 2H), 3.67 (brs, 2H), 2.86 (t, J = 6.61 Hz, 2H), 2.50-2.46 (m, 2H), 2.38-2.33 (m, 2H), 2.23-2.19 (m, 2H), 1.99-1.94 (m, 2H), 1.79-1.74 (m, 2H). |

Example 2

Compound 4

[3-({3-(3-furyl)-4-[(5-phenylpentyl)oxy]benzyl}amino)propyl]phosphonic acid

Step-1:

A mixture of Intermediate 1 (290 mg, 0.87 mmol) in DMF (12 mL) was reacted with furan-3-yl boronic acid [CAS 5552-70-0] (195 mg, 1.74 mmol) Na$_2$CO$_3$ (2.8 mL, 2M) and PdCl$_2$(PPh$_3$)$_2$ (69 mg, ~11 mol %) at 120° C. for 20 m with MWI (microwave irradiation: Biotage Initiator 2.5). The reaction mixture was diluted with water, and extracted (two times) with 1:1 EtOAc:Hexanes (200 mL). The organic layers were washed with water (three times), dried over MgSO$_4$, filtered and concentrated onto silica gel. Auto-column (9 hexane/1 EtOAc) gave Intermediate 3: 3-(furan-3-yl)-4-((5-phenylpentyl)oxy)benzaldehyde 230 mg (29%).

$^1$H NMR (300 MHz, CDCl$_3$): δ 9.92 (s, 1H), 8.03 (d, J=2.4 Hz, 1H), 7.75-7.72 (m, 1H), 7.48 (s, 15H), 7.30-7.16 (m, 3H), 7.19-7.16 (m, 3H), 7.02 (d, J=8.7 Hz, 1H), 6.85 (d, J=1.2 Hz, 1H), 4.14 (t, J=6.3 Hz, 2H), 2.70-2.60 (m, 2H), 2.01-1.50 (series of m, 6H).

Step-2:

Intermediate 3 (230 mg, 0.66 mmol) used in the appropriate steps of Example 1 produced the title compound: [3-({3-(3-furyl)-4-[(5-phenylpentyl)oxy]benzyl}amino)propyl]phosphonic acid $^1$H NMR (600 MHz, CF$_3$CO$_2$D): δ 7.66 (d, J=1.8 Hz, 1H), 7.56-7.50 (m, 2H), 7.40-7.35 (m, 3H), 7.30 (d, J=7.8 Hz, 2H), 7.25 (t, J=7.2 Hz, 1H), 7.20 (d, J=8.4 Hz, 1H), 6.85-6.83 (m, 1H), 4.47 (brs, 2H), 4.28 (t, J=6.6 Hz, 2H), 3.56 (brs, 2H), 2.79 (t, J=7.2 Hz, 2H), 2.42-2.36 (m, 2H), 2.31-2.25 (m, 2H), 2.09-2.05 (m, 2H), 1.88-1.84 (m, 2H), 1.71-1.68 (m, 2H).

Compounds 5, 6, 7 and 8 were prepared from the corresponding benzaldehyde, boronic acid and 3-aminopropylphosphonic acid in a similar manner to the procedure described in Example 2 for Compound 4. The reagents used and the results are described below in Table 2.

TABLE 2

| Compound number | IUPAC name | Reagent(s) used | $^1$H NMR δ (ppm) for Compound |
|---|---|---|---|
| 5 | [3-({4-[(5-phenylpentyl)oxy]-3-(3-thienyl)benzyl}amino)propyl]phosphonic acid | thiophen-3-yl boronic acid [CAS 5552-70-0] | $^1$H NMR (600 MHz, CF$_3$CO$_2$D): δ 7.58 (d, J = 1.8 Hz, 1H), 7.45 (brs, 2H), 7.39 (dd, J = 1.8, 8.4 Hz, 1H), 7.36 (s, 1H), 7.31 (t, J = 7.2 Hz, 2H), 7.23 (d, J = 8.4 Hz, 2H), 7.19 (d, J = 8.4 Hz, 2H), 4.41 (t, J = 5.4 Hz, 2H), 4.20 (t, J = 6.0 Hz, 2H), 3.54-3.48 (m, 2H), 2.70 (t, J = 7.2 Hz, 2H), 2.35-2.30 (m, 2H), 2.25-2.20 (m, 2H), 1.94-1.91 (m, 2H), 1.77-1.74 (m, 2H), 1.58-1.55 (m, 2H). |
| 6 | [3-({4-[(5-phenylpentyl)oxy]-3-(2-thienyl)benzyl}amino)propyl]phosphonic acid | thiophen-2-yl boronic acid [CAS 13331-23-2] | $^1$H NMR (300 MHz, CD$_3$OD): δ 7.83 (s, 1H), 7.59-7.56 (m, 1H), 7.40-7.35 (m, 2H), 7.26-7.20 (m, 2H), 7.17-7.05 (m, 5H), 4.14-4.10 (m, 4H), 3.10 (t, J = 6.6 Hz, 2H), 2.63 (t, J = 7.8 Hz, 2H) 2.06-1.88 (m, 4H), 1.76-1.56 (m, 6H). |
| 7 | [3-({4-[3-(4-isobutyiphenyl)propoxy]-3-(2-thienyl)benzyl}amino)propyl]phosphonic acid | 4-(2-methylpropyl)-benzenepropanol [CAS 147598-21-8] thiophen-2-yl boronic acid [CAS 13331-23-2] | $^1$H NMR (300 MHz, CD$_3$OD): δ 7.84 (d, J = 1.8 Hz, 1H), 7.64 (dd, J = 0.9, 3.6 Hz, 1H), 7.43 (d, J = 4.8 Hz, 1H), 7.35 (dd, J = 2.1, 8.4 Hz, 1H), 7.11-7.00 (m, 6H), 4.07-4.00 (m, 4H), 3.03 (t, J = 6.3 Hz, 2H), 2.81 (t, J = 7.8 Hz, 2H), 2.41 (d, J = 6.9 Hz, 2H), 2.18-2.10 (m, 2H), 2.10-2.19 (m, 2H), 1.85-1.75 (m, 1H), 1.71-1.61 (m, 2H), 0.87 (d, J = 6.6 Hz, 6H). |
| 8 | [3-({3-cyclopent-1-en-1-yl-4-[(5-phenylpentyl)oxy]benzyl}amino)propyl]phosphonic acid | cyclopentenyl boronic acid [CAS 850036-28-1] | MS (M + H)$^+$ 457.35 |
| 9 | 2-({4-[(5-phenylpentyl)oxy]-3-(2-thienyl)benzyl}amino)ethyl dihydrogen phosphate | Intermediate 1 thiophen-2-yl boronic acid 2-aminoethyl dihydrogen phosphate | $^1$H NMR (600 MHz, CF$_3$COOD): δ 7.70 (d, J = 2.4 Hz, 1H), 7.41 (brs, 2H), 7.33 (dd, J = 1.8, 8.4 Hz, 1H), 7.22-7.20 (m, 2H), 7.15 (d, J = 7.2 Hz, 2H), 7.12-7.09 (m, 2H), 7.03 (s, 1H), 4.51-4.48 (m, 2H), 4.40 (d, J = 4.2 Hz, 2H), 4.16 (t, J = 6.6 Hz, 2H), 3.58-3.52 (m, 2H), 2.63 (t, J = 7.8 Hz, 2H), 1.95-1.92 (m, 2H), 1.712-1.58 (m, 2H), 1.59-1.55(m, 2H). |

TABLE 2-continued

| Compound number | IUPAC name | Reagent(s) used | $^1$H NMR δ (ppm) for Compound |
|---|---|---|---|
| 10 | 3-({4-[(5-phenylpentyl)oxy]-3-(2-thienyl)benzyl}amino)propane-1-sulfonic acid | Intermediate 1 thiophen-2-yl boronic acid 3-aminopropane-1-sulfonic acid | $^1$H NMR (600 MHz, CF$_3$COOD): δ 7.65 (brs, 1H), 7.36 (brs, 2H), 7.25 (d, J = 7.8 Hz, 1H), 7.20-7.18 (m, 2H), 7.13-7.12 (m, 2H), 7.10-7.05 (m, 2H), 7.01 (s, 1H), 4.30 (t, J = 5.4 Hz, 2H), 4.13 (t, J = 6.6, 2H), 3.52-3.50 (m, 2H), 3.42 (t, J= 6.6 Hz, 2H), 2.61 (t, J = 7.8 Hz, 2H), 2.46-2.40 (m, 2H), 1.84-1.89 (m, 2H), 1.72-1.67 (m, 2H), 1.58-1.53 (m, 2H). |
| 11 | methyl[3-({4-[(5-phenylpentyl)oxy]-3-(2-thienyl)benzyl}amino)propyl]phosphinic acid | Intermediate 1 thiophen-2-yl boronic acid (3-aminopropyl)(methyl)phosphinic acid | $^1$H NMR (600 MHz, CF$_3$COOD): δ 7.67 (d, J = 2.4 Hz, 1H), 7.45 (brs, 2H), 7.28 (dd, J = 2.4, 8.4 Hz, 1H), 7.23-7.21 (m, 2H), 7.16-7.15 (m, 2H), 7.13-7.08 (m, 2H), 7.04 (s, 1H), 4.26-4.33 (m, 2H), 4.17 (t, J = 6.0Hz, 2H), 3.46-3.39 (m, 2H), 2.64 (t, J = 7.2 Hz, 2H), 3.00-2.24 (m, 2H), 2.13-2.08 (m, 2H), 1.97-1.92 (m, 2H), 1.75-1.69 (m, 5H), 1.61-1.56 (m, 2H). |
| 12 | 2-({4-[(5-phenylpentyl)oxy]-3-(2-thienyl)benzyl}amino)propan-1-ol | Intermediate 1 thiophen-2-yl boronic acid 2-aminopropan-1-ol | $^1$H NMR (600 MHz, CDCl$_3$): δ 7.60 (d, J = 1.8 Hz, 1H), 7.50 (dd, J = 1.2, 4.2 Hz, 1H), 7.31 (dd, J = 1.2, 5.4 Hz, 1H), 7.27 (t, J = 7.8 Hz, 2H), 7.20-7.17 (m, 4H), 7.07 (dd, J = 3.6, 4.8 Hz, 1H), 6.91 (d, J = 8.4 Hz, 1H), 4.06 (t, J = 6.6 Hz, 2H), 3.86 (d, J = 12.6 Hz, 1H), 3.72 (d, J = 12.6 Hz, 1H), 3.63-3.61 (m, 1H), 3.49 (s, 2H), 3.31-3.28 (m, 1H), 2.89-2.86 (m,1H), 2.65 (t, J = 7.8 Hz, 2H), 1.94-1.89 (m, 2H), 1.74-1.69 (m, 2H), 1.60-1.55 (m, 2H), 1.11 (d, J = 6.6 Hz, 3H) |
| 13 | 2-({4-[(5-phenylpentyl)oxy]-3-(2-thienyl)benzyl}amino)propane-1,3-diol | Intermediate 1 thiophen-2-yl boronic acid 2-aminopropane-1,3-diol | $^1$H NMR (600 MHz, CDCl$_3$): δ 7.62 (d, J = 2.1 Hz, 1H), 7.51 (dd, J = 1.2, 3.6 Hz, 1H), 7.31 (dd, J = 1.2, 5.4 Hz, 1H), 7.28-7.25 (m, 2H), 7.22-7.17 (m, 4H), 7.07 (dd, J = 3.6, 5.1 Hz, 1H), 6.91 (d, J = 8.1 Hz, 1H), 4.06 (t, J = 6.3 Hz, 2H), 3.84 (s, 2H), 3.78-3.73 (m, 2H), 3.65-3.60 (m, 2H), 2.88-2.83 (m, 1H), 2.65 (t, J = 7.2 Hz, 2H), 2.19 (brs, 3H), 1.96-1.87 (m, 2H), 1.75-1.66 (m, 2H), 1.62-1.54 (m, 2H). |

Example 3

Compound 14

{3-[({6-(3-furyl)-5-[(5-phenylpentyl)oxy]pyridin-2-yl}methyl)amino]propyl}phosphonic acid Step-1:

A solution of 2-bromo-6-(hydroxymethyl)pyridin-3-ol [CAS 168015-04-1](~1 g, ~5 mmol) in dioxane (100 mL) was treated with MnO$_2$ (3.0 g, 29.3 mmol, 85%) at 100° C. for 16-18 h. The mixture was filtered, and concentrated onto silica gel. Auto-column (7:3 hexane/EtOAc gave Intermediate 4: 6-bromo-5-hydroxypicolinaldehyde as a solid 0.6 g (60%). $^1$H NMR (300 MHz, CDCl$_3$): δ 9.91 (s, 1H), 7.92 (d, 4.2 Hz, 1H), 7.43 (d, 4.2 Hz, 1H)

Step-2:

Reaction of Intermediate 4 (0.59 g, 2.92 mmol) and (5-bromopentyl)benzene [CAS 14469-83-1] (0.80 g, 3.52 mmol) and K$_2$CO$_3$ (0.8 g, 5.79 mmol) in DMF (15 mL) at 100° C. for 4 h followed by a standard aqueous work-up and auto-column purification gave the product Intermediate 5: 6-bromo-5-(5-phenylpentyloxy)picolinaldehyde as a clear oil (0.67 g (66%). $^1$H NMR (300 MHz, CDCl$_3$): δ 9.93 (s, 1H), 7.92 9 s, J=8.1 Hz, 1H), 7.28-7.18 (m, 6H), 4.12 (t, J=6.0 Hz, 2H), 2.67 (t, J=7.2 Hz, 2H), 1.93-1.55 (series of m, 6H).

Step-3:

Intermediate 5 (0.335 g, 0.96 mmol) and furan-3-yl boronic acid [CAS 5552-70-0] (0.215 g, 1.92 mmol), Na$_2$CO$_3$ (2.8 mL, 2M) in DMF (12 mL) with PdCl$_2$(PPh$_3$)$_2$ (74 mg, ~11 mol %) at 120° C. for 20 m with MWI (microwave irradiation: Biotage Initiator 2.5). The reaction mixture was diluted with water, and extracted (three times) with 1:1 EtOAc:Hexanes. The organic layers were dried over MgSO$_4$, filtered and concentrated onto silica gel. Auto-column (9 hexane/1 EtOAc) gave Intermediate 6: 6-(furan-3-yl)-5-((5-phenylpentyl)oxy)picolinaldehyde. $^1$H NMR (300 MHz, CDCl$_3$): δ 10.0 (s, 1H), 8.21 (s, 1H), 7.84 (d, J=8.4 Hz, 1H), 7.50 (brs, 1H), 7.28-7.17 (series of m, 7H), 4.16 (t, J=6.3 Hz, 2H), 2.67 (t, J=9.0 Hz, 2H), 1.99-1.55 (series of m, 6H).

Use of Intermediate 6 in the appropriate steps of Example 1 produced the title compound; {3-[({6-(3-furyl)-5-[(5-phenylpentyl)oxy]pyridin-2-yl}methyl)amino]propyl} phosphonic acid 0.17 g (53%)

$^1$H NMR (600 MHz, CF$_3$CO$_2$D): δ 8.57 (s, 1H), 8.60-8.30 (m, 2H), 7.73 (s, 1H), 7.30 (t, J=7.2 Hz, 2H), 7.21-7.18 (m, 2H), 4.95 (s, 2H), 4.46 (t, J=6.0 Hz, 2H), 3.68 (t, J=6.6 Hz, 2H), 2.75 (t, J=7.8 Hz, 2H), 2.45-2.40 (m, 2H), 2.31-2.27 (m, 2H), 2.15-2.12 (m, 2H), 1.87-1.84 (m, 2H), 1.69-1.65 (m, 2H).

Compounds 15, 16 and 17 were prepared from the corresponding staring materials and 3-aminopropylphosphonic acid in a similar manner to the procedure described in Example 3 for Compound 14. The reagents used and the results are described below in Table 3.

TABLE 3

| Compound number | IUPAC name | Reagent(s) used | $^1$H NMR δ (ppm) for Compound |
|---|---|---|---|
| 15 | {3-[({5-[(5-phenylpentyl)oxy]-6-(2-thienyl)pyridin-2-yl}methyl)amino]propyl} phosphonic acid | thiophen-2-yl boronic acid [CAS 13331-23-2] | $^1$H NMR (600 MHz, CF$_3$CO$_2$D): δ 8.29 (d, J = 3.6 Hz, 1H), 8.14-8.09 (m, 3H), 7.50 (t, J = 4.81 Hz, 1H), 7.42-7.38 (m, 2H), 7.35-7.30 (m, 3H), 5.06 (s, 2H), 4.57 (t, J = 6.0 Hz, 2H), 3.79 (t, 6.6 Hz, 2H), 2.86 t(, J = 6.6 Hz, 2H), 2.55-2.50 (m, 2H), 2.41-2.36 (m, 2H), 2.55-2.23 (m, 2H), 1.98-1.94 (m, 2H), 1.70-1.60 (m, 2H). |
| 16 | (3-{[4-(nonyloxy)-3-(2-thienyl) benzyl]amino} propyl)phosphonic acid | 3-bromo-4-hydroxybenzaldehyde [CAS 2973-78-6] 1-bromononane [CAS 693-58-3] tributyl(thiophen-2-yl)stannane [CAS 54663-78-4] | $^1$H NMR (600 MHz, CF$_3$CO$_2$D): δ 7.68 (s, 1H), 7.51-7.38 (m, 2H), 7.29 (d, J = 3.9 Hz, 1H), 7.13 (dd, J = 1.2, 8.4 Hz, 1H), 7.07 (d, J = 1.8 Hz, 1H), 4.35 (s, 2H), 4.20-4.18 (m, 2H), 3.44 (s, 2H), 2.30-2.22 (m, 2H), 2.20-2.10 (m, 2H), 1.93 (t, J = 6.0 Hz, 2H), 1.56-1.53 (m, 2H), 1.40-1.29 (m, 10H), 0.87-0.85 (m, 3H). |
| 17 | (3-{[4-(decyloxy)-3-(2-thienyl) benzyl]amino} propyl)phosphonic acid | 3-bromo-4-hydroxybenzaldehyde [CAS 2973-78-6] 1-bromodecane [CAS 112-29-8] tributyl(thiophen-2-yl)stannane [CAS 54663-78-4] | $^1$H NMR (600 MHz, CF$_3$CO$_2$D): δ 7.74 (s, 1H), 7.35 (d, J = 8.4 Hz, 1H), 7.19 (d, J = 8.4 Hz, 1H), 7.13 (s, 1H), 4.40 (s, 2H), 4.25 (t, J = 6.6 Hz, 2H), 3.49 (t, J = 6.6 Hz, 2H), 2.35-2.29 (m, 2H), 2.23-2.18 (m, 2H), 2.01-1.97 (m, 2H), 1.62-1.58 (m, 2H), 1.47-1.34 (m, 2H), 0.92 (t, J = 7.2 Hz, 3H). |

Example 4

Compound 18

3-({3-(5-fluoro-2-thienyl)-4-[(5-phenylpentyl)oxy] benzyl}amino)propyl]phosphonic acid The following experimental describes methods used for preparation of 3-(5-fluorothiophen-2-yl)-4-((5-phenylpentyl)oxy)benzaldehyde (Intermediate 10)

Proton NMR (nuclear magnetic resonance) spectra were taken either at 60 MHz on a Varian T-60 spectrometer or at 300 MHz on a Varian Inova system. The spectra of all products were consistent with their structures. Reverse-phase HPLC analyses of products were performed on an Agilent 1100 instrument using an Zorbax SB-phenyl column (250× 4.6 mm), with a flow rate at 1.0 mL/min. The elution was isocratic at 40 C. using a mixture of A1 (700 mL of water, 300 mL of methanol, and 3 mL of Et$_3$N adjusted to pH 3.4 with H$_3$PO$_4$), and methanol. Conditions: A1:CH$_3$OH (10:90). The retention times were as follows: 4,4,5,5-tetramethyl-2-(4-((5-phenylpentyl)oxy)-3-(thiophen-2-yl)phenyl)-1,3-dioxolane, 5.36 min; 2-(3-(5-fluorothiophen-2-yl)-4-((5-phenylpentyl)oxy)phenyl)-4,4,5,5-tetramethyl-1,3-dioxolane, 5.54 min; and for 3-(5-fluorothiophen-2-yl)-4-((5-phenylpentyl)oxy) benzaldehyde, 5.0 min. Thin layer chromatography (TLC) made use of E. Merck Kieselgel PF60 plates. TLC solvent systems are indicated in the text.

Intermediate-1 and thiophen-2-yl boronic acid, [CAS 13331-23-2] were used in the appropriate procedural steps of Example 2 for Compound 6 to produce 4-((5-phenylpentyl) oxy)-3-(thiophen-2-yl)benzaldehyde (Intermediate 7).

Step-1:

In a 500 mL 3-necked flask equipped with a stir-bar and condenser was placed 4-((5-phenylpentyl)oxy)-3-(thiophen-2-yl)benzaldehyde (Intermediate 7) (4.9 g, 1.4 mmol), pinacol (6.6 g, 5.6 mol) and p-toluenesulfonic acid (0.8 g, 4.2 mmol) in benzene (125 mL). The resulting mixture was refluxed for 1 h. TLC analysis (EtOAc:hexane; 1:1) showed the reaction was complete. The reaction was cooled to room temperature, washed with saturated NaHCO$_3$ (2×75 mL), brine (1×75 mL), filtered through 1 PS filter paper and concentrated under reduced pressure to give a brown oil. The oil was flash chromatographed over silica gel (100 g) with anhydrous sodium sulfate (20 g) on top packed with hexane. The column was eluted with 12×50 mL of 15% EtOAc in hexane. The product was eluted to give 5.1 g (81%) 4,4,5,5-tetramethyl-2-(4-((5-phenylpentyl)oxy)-3-(thiophen-2-yl)phenyl)-1,3-dioxolane (Intermediate 8) as a yellow oil. HPLC analysis showed a purity of ~97%. NMR (CDCl$_3$) δ 7.8 (s, 1H), 7.55 (d, 1H), 7.1-7.4 (m, 8H), 6.95 (d, 1H), 6.0 (s, 1H), 4.1 (t, 2H), 2.7 (t, 2H), 1.95 (m, 2H), 1.7 (m, 2H), 1.6 (m, 2H), 1.35 (d, 12H).

Step-2:

In a 500 mL 3-necked flask equipped with a stir-bar, dropping funnel, and thermometer was placed 4,4,5,5-tetramethyl-2-(4-((5-phenylpentyl)oxy)-3-(thiophen-2-yl)phenyl)-1,3-dioxolane (Intermediate 8) (4.95 g, 1.1 mmol) in tetrahydrofuran (100 mL) under argon. The resulting solution was cooled to −78° C. n-BuLi (8.8 mL, 2.2 mmol of 2.5 M in hexane) was added over 30 min. The mixture was stirred for 90 m and then N-fluorobenzenesulfonimide (7.5 g, 2.4 mmol) was added as powder in one portion. To the reaction mixture was added saturated ammonium chloride (75 mL), water (25 mL) and ethyl acetate (100 mL) after stirring for 90 m at −78° C. The reaction mixture was warmed to room temperature. The organic layer was separated, washed with brine (1×75 mL), filtered through 1 PS filter paper and concentrated under reduced pressure to give 11.5 g of a green residue. The residue was triturated with 10% EtOAc in hexane (50 mL). The insoluble material was filtered and filtrate concentrated under reduced pressure to give 6.5 g of a green residue. The residue was flash chromatographed repeatedly over silica gel with anhydrous sodium sulfate on top; the columns were eluted with either EtOAc:hexanes and/or hexanes:$CH_2Cl_2$ to give 2.9 g (57%) of 2-(3-(5-fluorothiophen-2-yl)-4-((5-phenylpentyl)oxy)phenyl)-4,4,5,5-tetramethyl-1,3-dioxolane (Intermediate 9) as colorless oil. HPLC analysis showed a purity of ~98%.

NMR ($CDCl_3$) δ 7.75 (s, 1H), 7.2-7.4 (m, 6H), 7.15 (t, 1H), 6.95 (d, 1H), 6.45 (t, 1H), 6.0 (s, 1H), 4.15 (t, 2H), 2.7 (t, 2H), 1.95 (m, 2H), 1.75 (m, 2H), 1.6 (m, 2H), 1.35 (d, 12H).

Step-3:

A solution of 2-(3-(5-fluorothiophen-2-yl)-4-((5-phenylpentyl)oxy)phenyl)-4,4,5,5-tetramethyl-1,3-dioxolane (Intermediate 9) (2.01 g, 4.3 mmol) in tetrahydrofuran (50 mL) and 3 M HCl (50 mL) was stirred at rt, overnight. To the reaction mixture was diluted with ethyl acetate (50 mL) and water (50 mL). The organic layer was separated, washed with brine (1×50 mL), filtered through 1 PS filter paper and concentrated under reduced pressure to give 1.6 g of an oil. The oil was dissolved in boiling hexane (20 mL) and after standing for 2 h, a white crystalline solid was collected; and dried under vacuum to give 1.15 g (73%) of Intermediate 10: 3-(5-fluorothiophen-2-yl)-4-((5-phenylpentyl)oxy)benzaldehyde, HPLC analysis showed a purity of ~99%.

$^{19}F$ NMR showed a quartet at −131.201, −131.209, −131.215 and −131.223. Use of Intermediate 10 in the procedure of Example 1 produced the title compound [3-({3-(5-fluoro-2-thienyl)-4-[(5-phenylpentyl)oxy]benzyl}amino) propyl]phosphonic acid.

$^1H$ NMR (600 MHz, $CF_3CO_2D$): δ 7.57 (d, J=1.8 Hz, 1H), 7.23-7.18 (m, 3H), 7.14 (d, J=6.6 Hz, 2H), 7.08 (t, J=7.2 Hz, 1H), 7.03-7.01 (m, 2H), 6.38-6.37 (m, 1H), 4.30 (t, J=5.4 Hz, 2H), 4.13 (t, J=6.6 Hz, 2H), 3.44-3.36 (m, 2H), 2.63 (t, J=7.8 Hz, 2H), 2.25-2.22 (m, 2H), 2.15-2.10 (m, 2H), 1.95-1.92 (m, 2H), 1.74-1.68 (m, 2H), 1.58-1.55 (m, 2H).

Example 5

Biological Data

Compounds were synthesized and tested for S1P1 activity using the GTP $\gamma^{35}S$ binding assay. These compounds may be assessed for their ability to activate or block activation of the human S1P1 receptor in cells stably expressing the S1P1 receptor. GTP $\gamma^{35}S$ binding was measured in the medium containing (mM) HEPES 25, pH 7.4, $MgCl_2$ 10, NaCl 100, dithitothreitol 0.5, digitonin 0.003%, 0.2 nM GTP $\gamma^{35}S$, and 5 μg membrane protein in a volume of 150 μl. Test compounds were included in the concentration range from 0.08 to 5,000 nM unless indicated otherwise. Membranes were incubated with 100 μM 5'-adenylylimmidodiphosphate for 30 min, and subsequently with 10 μM GDP for 10 min on ice. Drug solutions and membrane were mixed, and then reactions were initiated by adding GTP $\gamma^{35}S$ and continued for 30 min at 25° C. Reaction mixtures were filtered over Whatman GF/B filters under vacuum, and washed three times with 3 mL of ice-cold buffer (HEPES 25, pH7.4, $MgCl_2$ 10 and NaCl 100). Filters were dried and mixed with scintillant, and counted for $^{35}S$ activity using a β-counter. Agonist-induced GTP $\gamma^{35}S$ binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

Table 1 shows activity potency: S1P1 receptor from GTP $\gamma^{35}S$: nM, ($EC_{50}$), % stimulation.

Activity potency: S1P1 receptor from GTP $\gamma^{35}S$: nM, ($EC_{50}$).

TABLE 2

| Compound number | IUPAC name | S1P1 $EC_{50}$ (nM) |
|---|---|---|
| 6 | [3-({4-[(5-phenylpentyl)oxy]-3-(2-thienyl)benzyl}amino)propyl]phosphonic acid | 1 |
| 7 | [3-({4-[3-(4-isobutylphenyl)propoxy]-3-(2-thienyl)benzyl}amino)propyl]phosphonic acid | 15 |
| 8 | [3-({3-cyclopent-1-en-1-yl-4-[(5-phenylpentyl)oxy]benzyl}amino)propyl]phosphonic acid | 3 |
| 10 | {3-[({5-[(5-phenylpentyl)oxy]-6-(2-thienyl) pyridin-2-yl}methyl)amino]propyl} | 1 |
| 12 | phosphonic acid(3-{[4-(decyloxy)-3-(2-thienyl)benzyl]amino}propyl)phosphonic acid | 294 |

Example 6

Lymphopenia Assay in Mice

Test drugs are prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples are obtained by puncturing the submandibular skin with a Goldenrod animal lancet at 5, 24, 48, 72, and 96 hrs post drug application. Blood is collected into microvettes (SARSTEDT) containing EDTA tripotassium salt. Lymphocytes in blood samples are counted using a HEMAVET Multispecies Hematology System, HEMAVET HV950FS (Drew Scientific Inc.). (Hale, J. et al Bioorg. & Med. Chem. Lett. 14 (2004) 3351).

Detailed Description of FIG. 1

A lymphopenia assay in mice; as previously described, was employed to measure the in vivo blood lymphocyte depletion after dosing with [3-({4-[(5-phenylpentyl)oxy]-3-(2-thienyl) benzyl}amino)propyl]phosphonic acid. This S1P1 agonist is useful for S1P-related diseases and exemplified by the lymphopenia in vivo response. Test drug, with [3-({4-[(5-phenylpentyl)oxy]-3-(2-thienyl)benzyl}amino)propyl]phosphonic acid was prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples were obtained by puncturing the submandibular skin with a Goldenrod animal lancet at 24, 48, and 72 hrs post drug application. Blood was collected into microvettes (SARSTEDT) containing EDTA tripotassium salt. Lymphocytes in blood samples were counted using a HEMAVET Multispecies Hematology System, HEMAVET HV950FS (Drew Scientific Inc.). Results are shown in the FIG. 1 that depicts lowered lymphocyte count after 5 hours (<1 number of lymphocytes $10^3$/μL blood).

What is claimed is:

1. A method of treating a disorder associated with sphingosine-1-phosphate (S1P) receptor modulation, which comprises administering to a mammal in need thereof, a pharmaceutical composition comprising a therapeutically effective amount of at least one compound of Formula I

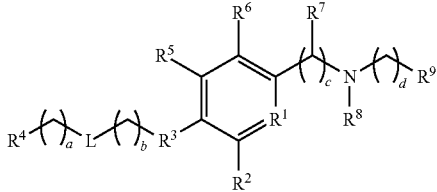

Formula I wherein:
$R^1$ is N or C—$R^{10}$;
$R^2$ is aromatic heterocycle, non-aromatic heterocycle, cycloalkyl, cycloalkenyl or aryl;
$R^3$ is O;
$R^4$ is H or aryl;
$R^5$ is H, halogen, —$OC_{1-3}$ alkyl;
$R^6$ is H, halogen or $C_{1-3}$ alkyl;
$R^7$ is H or $C_{1-6}$ alkyl;
$R^8$ is H;
$R^9$ is —$OPO_3H_2$, —$P(O)(OH)_2$, —$S(O)_2OH$, —$P(O)MeOH$, or —$OR^{15}$;
$R^{10}$ is H, $C_{1-6}$ alkyl;
$R^{15}$ is H or $C_{1-3}$ alkyl;
L is $CHR^{16}$;
a is 0, 1, 2, 3, 4 or 5;
b is 0, 1, 2, 3, 4 or 5;
c is 0 or 1;
d is 0, 1, 2 or 3;
$R^{16}$ is H, $C_{1-3}$ alkyl, —$OC_{1-3}$ alkyl, halogen, hydroxyl or amino, and
with the proviso:
when $R^9$ is $OR^{15}$ then d is not 1.

2. A method of claim 1, wherein the mammal is a human.

* * * * *

UNITED STATES PATENT AND TRADEMARK OFFICE
CERTIFICATE OF CORRECTION

PATENT NO. : 8,703,745 B1
APPLICATION NO. : 13/773189
DATED : April 22, 2014
INVENTOR(S) : Todd M. Heidelbaugh et al.

It is certified that error appears in the above-identified patent and that said Letters Patent is hereby corrected as shown below:

On the title page, Item (72), under "Inventors", in column 1, line 2, delete "AR (US);" and insert -- CA (US); --, therefor.

On title page 2, in column 1, Item (56), under "Other Publications", line 12, delete "-y1)-" and insert -- -yl)- --, therefor.

In the Specification

In column 1, line 25, delete "Sphingosine-1 phosphate" and insert -- Sphingosine-1-phosphate --, therefor.

In column 2, line 34, delete "$R^{19}$" and insert -- $R^{10}$ --, therefor.

In column 2, line 59, delete "atom." and insert -- atoms. --, therefor.

In column 4, line 27, delete "CH—$R^{12}$," and insert -- —CH—$R^{12}$, --, therefor.

In column 4, line 34, delete "alky." and insert -- alkyl. --, therefor.

In column 4, line 47, delete "alkyl" and insert -- alkyl. --, therefor.

In column 4, line 67, delete "—C≡O—:" and insert -- —C≡C—: --, therefor.

In column 5, line 36, delete "—C≡O—:" and insert -- —C≡C—: --, therefor.

In column 6, line 12, delete "—C≡O—:" and insert -- —C≡C—: --, therefor.

In column 6, line 48, delete "—C≡O—:" and insert -- —C≡C—: --, therefor.

In column 7, line 13, delete "—C≡O—:" and insert -- —C≡C—: --, therefor.

In column 7, line 44, delete "—C≡O—:" and insert -- —C≡C—: --, therefor.

In column 9, line 67, delete "methylsulfonic," and insert -- methanesulfonic, --, therefor.

In column 10, line 2, delete "Stahal" and insert -- Stahl --, therefor.

In column 10, line 3, delete "Chemica" and insert -- Chimica --, therefor.

In column 10, line 52, delete "antoimmune" and insert -- autoimmune --, therefor.

Signed and Sealed this
Seventh Day of October, 2014

Michelle K. Lee
*Deputy Director of the United States Patent and Trademark Office*

In column 10, line 53, delete "dermititis," and insert -- dermatitis, --, therefor.

In column 11, lines 32-33, delete "antoimmune" and insert -- autoimmune --, therefor.

In column 11, line 34, delete "dermititis," and insert -- dermatitis, --, therefor.

In column 12, line 38, delete "known to" and insert -- known in --, therefor.

In column 13, line 32, delete "and or" and insert -- and/or --, therefor.

In column 14, lines 27-35, delete " 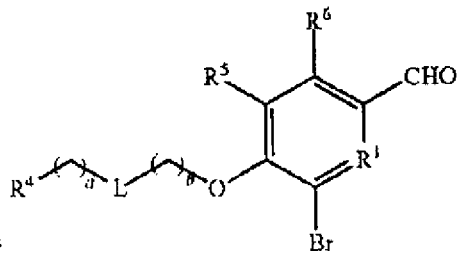 " and insert -- 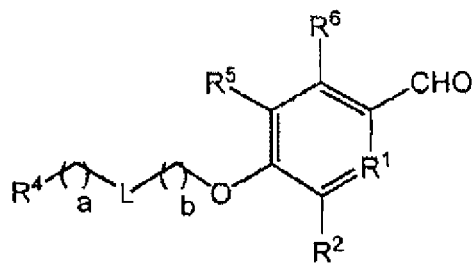 --, therefor.

In column 15, lines 27-35, delete " 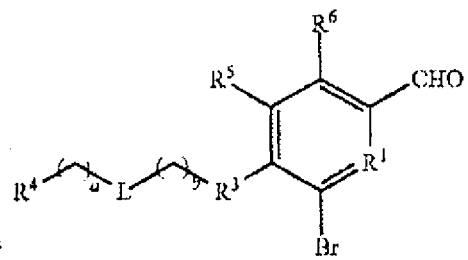 " and insert -- 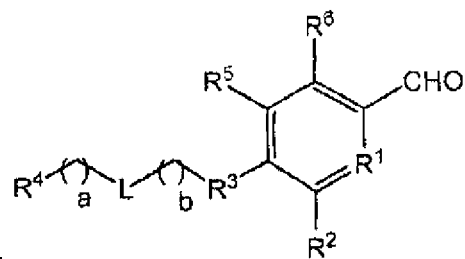 --, therefor.

In column 15, line 53, delete "CH" and insert -- N --, therefor.

In column 16, line 31, delete "diasteroisomeric" and insert -- diastereoisomeric --, therefor.

In column 16, line 47, delete "AscentScientific" and insert -- Ascent Scientific --, therefor.

In column 16, line 48, delete "Ukrorgsynth," and insert -- Ukrorgsynthesis, --, therefor.

In column 16, line 49, delete "Syn Chem," and insert -- SynChem, --, therefor.

In column 17, line 20, delete "magnesiunm" and insert -- magnesium --, therefor.

In column 18, line 28, delete "(52%)" and insert -- (52%). --, therefor.

CERTIFICATE OF CORRECTION (continued)
U.S. Pat. No. 8,703,745 B1

In column 19, line 46, delete "acid" and insert -- acid. --, therefor.

In column 21, line 54, delete "3H)" and insert -- 3H). --, therefor.

In column 22, line 28, delete "1H)" and insert -- 1H). --, therefor.

In column 22, line 56, delete "(53%)" and insert -- (53%). --, therefor.

In column 24, line 10, delete "10)" and insert -- 10). --, therefor.

In column 24, line 18, delete "40C." and insert -- 40°C. --, therefor.

In column 25, line 52, delete "dithitothreitol" and insert -- dithiothreitol --, therefor.

In column 25, line 56, delete "5'-adenylylimmidodiphosphate" and insert -- 5'-adenylylimidodiphosphate --, therefor.

In column 25, line 62, delete "pH7.4," and insert -- pH 7.4, --, therefor.

In the Claims

In column 28, line 3, in claim 1, delete "—$OC_{1-3}$ alkyl;" and insert -- hydroxyl or $OC_{1-3}$ alkyl; --, therefor.